United States Patent

Von Sprecher et al.

Patent Number: 5,604,247
Date of Patent: Feb. 18, 1997

[54] CHROMONE DERIVATIVES

[75] Inventors: Andreas Von Sprecher, Oberwil; Marc Gerspacher, Brugg; Robert Mah, Allschwil; Silvio Roggo, Muttenz; Walter Schilling, Himmelried; Silvio Ofner, Münchenstein; Siem J. Veenstra, Basel, all of Switzerland

[73] Assignee: Ciba-Geigy Corporation, Tarrytown, N.Y.

[21] Appl. No.: 632,971

[22] Filed: Apr. 16, 1996

[30] Foreign Application Priority Data

Apr. 24, 1995 [CH] Switzerland .................. 1157/95

[51] Int. Cl.$^6$ .................. A61K 31/445; G07D 405/12
[52] U.S. Cl. .................. 514/320; 546/196
[58] Field of Search .................. 546/196; 514/320

[56] References Cited

U.S. PATENT DOCUMENTS 5,310,743  5/1994  Schilling et al. .................. 514/311

FOREIGN PATENT DOCUMENTS 9511895  5/1995  WIPO .

*Primary Examiner*—Johann Richter
*Assistant Examiner*—Barbara Badio
*Attorney, Agent, or Firm*—Marla J. Mathias; Gregory D. Ferraro

[57] ABSTRACT

Compounds of formula I

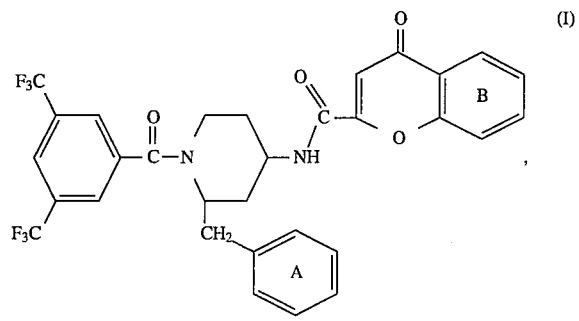

wherein rings A and B are as defined in the specification, have valuable pharmacological properties and are particularly effective as NK1 antagonists and substance P antagonists. Said compounds are prepared in a manner known per se.

10 Claims, No Drawings

CHROMONE DERIVATIVES

The present invention relates to compounds of formula I

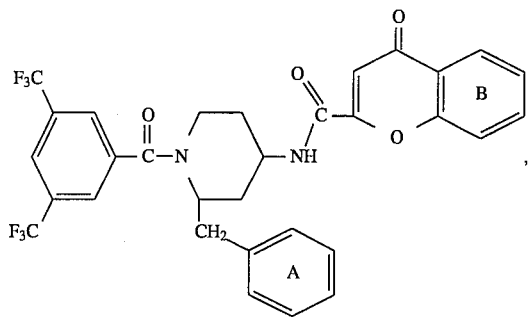

wherein ring A is unsubstituted or substituted and ring B is unsubstituted or substituted. These compounds have valuable pharmacological properties and are particularly effective as neurokinine 1 antagonists and substance P antagonists.

The invention relates in particular to those compounds of formula I wherein ring A is unsubstituted or monosubstituted by lower alkyl, lower alkoxy, halogen, nitro or trifluoromethyl and ring B is unsubstituted or substituted by 1–4 substituents selected from the group consisting of lower alkyl, hydroxy, lower alkoxy, lower alkylthio, halogen, nitro, cyano and trifluoromethyl as well as to salts thereof, to processes for the preparation of these compounds, to pharmaceutical compositions comprising these compounds, to the use of these compounds for the therapeutic treatment of the human or animal body or for the preparation of pharmaceutical compositions.

Since the compounds of this invention contain at least two optically active carbon atoms, they can accordingly be present in the form of stereoisomers, stereoisomer mixtures as well as in the form of the (substantially) pure diastereoisomers. The invention also embraces corresponding stereoisomers. The compounds of formula I are preferably in the diastereoisomeric form as represented in formula Ia:

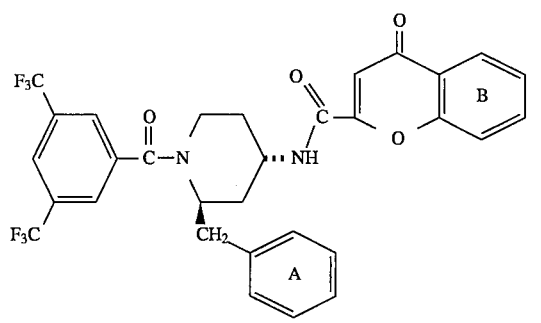

If not defined otherwise, the general terms used hereinbefore and hereinafter have the following meanings.

The term "lower" means that corresponding groups and compounds each contain 1 up to and including 7, preferably 1 up to and including 4, carbon atoms.

Lower alkyl is typically methyl, ethyl, n-propyl, isopropyl, n-butyl, isobutyl, sec-butyl, tert-butyl or a corresponding pentyl, hexyl or heptyl radical. $C_1$–$C_4$Alkyl is preferred.

Lower alkoxy is typically methoxy, ethoxy, n-propyloxy, isopropyloxy, n-butyloxy, isobutyloxy, sec-butyloxy, tert-butyloxy or a corresponding pentyloxy, hexyloxy or heptyloxy radical. $C_1$–$C_4$Alkoxy is preferred.

Halogen is typically fluoro, chloro or bromo, but can also be iodo. Chloro is preferred.

The compounds of formula I can be in the form of salts, preferably in the form of pharmaceutically acceptable salts. Acid addition salts can be formed with the basic center of the piperidine ring. Suitable acid components may be, for example, strong inorganic acids, typically mineral acids, e.g. sulfuric acid, phosphoric acids, e.g. orthophosphoric acid, hydrohalic acids, e.g. hydrochloric acid, or strong organic carboxylic acids, typically lower alkanecarboxylic acids which may be substituted, e.g. by halogen, such as acetic acid or trifluoroacetic acid, dicacarboxylic acids which may be unsaturated, e.g. oxalic, malonic, succinic, maleic, fumaric, phthalic or terephthalic acid, hydroxycarboxylic acids, e.g. ascorbic, glycolic, lactic, malic, tartaric or citric acid, amino acids, e.g. aspartic or glutaminic acid, or benzoic acid, or organic sulfonic acids, typically lower alkanesulfonic acids which may be substituted, e.g. by halogen, typically methanesulfonic acid, or arylsulfonic acids which may be substituted, e.g. by lower alkyl, typically p-toluenesulfonic acid. Also included are salts which are not suitable for therapeutic use but which may be used, for example, for isolating or purifying free compounds of formula I or their pharmaceutically acceptable salts. Only the pharmaceutically acceptable non-toxic salts are used for therapeutic application and are therefore preferred.

The compounds of formula I—including their pharmaceutically acceptable salts which hereinafter will always be included—have valuable pharmacological properties. They act in particular as neurokinine 1 antagonists (NK1 antagonists) and accordingly they are capable of preventing symptoms that are caused, inter alia, by the release of substance P.

The respiratory tract has sensory nerves containing a number of neuropeptides, in particular tachykinines and CGRP (=calcitonin gene-related peptides). The activation of the sensory nerves results in a local release of neuropeptides within the lung. Substance P and neurokinine A are mainly released which trigger an acute inflammatory reaction called neurogenic inflammation. This inflammatory reaction proceeds mainly via NK1 receptor activation and includes in particular vasodilatation, microvascular leaks, recruitment of inflammatory leukocytes and excessive secretion of mucus. These substance P effects are typical symptoms of asthma.

The pharmacological effect of the compounds of formula I is based in particular on the antagonization of the NK1 receptor. The compounds of formula I are also capable of inhibiting the neurogenic inflammation as well as the tachykinine-induced broncho-constriction.

The advantageous effect of the compounds of formula I can be demonstrated by different in vitro or in vivo test methods. For example in the in vivo NK1 bronchospasm test on guinea pigs having ED50 values, oral doses of from about 0.03 mg/kg are effective, the test substances being administered 2, 4 or 24 hours prior to the intravenous administration of 3.0 µg/kg [Sar9,Met(O2)11]-substance P [=SarSP]. The challenge with SarSP induces an increase of the intratracheal pressure in the guinea pig. The compounds of this invention are distinguished by extremely good oral activity as well as by an unusually long duration of efficacy.

As antagonists of the NK1 receptors, the compounds of formula I are therapeutically useful in the prevention, treatment or diagnosis of a number of diseases, for example: diseases of the upper and the lower respiratory tract, such as bronchial asthma, allergic asthma, non-allergic asthma, allergic hypersensitivity and hypersecretive conditions, e.g. chronic bronchitis and cystic fibrosis; fibrosis of the lung of various etiology; diseases of the pulmonary and bronchial circulation, such as pulmonary hypertension, angiogenesis, metastases; diseases of the gastrointestinal tract, such as Crohn's disease, Hirsprung's disease, diarrhea, malabsorptive conditions, inflammatory conditions; affective, traumatic or inflammatory disruptions of the central and peripheral nervous system, such as depressions, anxieties, migraine and other forms of cranial pain, apoplexies, emesis; diseases of the blood vessels, e.g. the cranial vessels; diseases relating to the microcirculation in diverse tissues such as the skin and eyes; diseases of the immune systems and the reticulohistiocytary system, e.g. in the splenic and lymphatic tissues; conditions of pain and other diseases involving the activity of neurokinines, tachykinines or other related substances in their pathogenesis, pathology and etiology.

Substance P is a naturally occurring undecapeptide of the tachykinine family. It is produced in the mammalian organism and acts pharmacologically as neuropeptide. Substance P plays an important part in a variety of diseases, for example in conditions of pain, in migraine and in some disorders of the central nervous system, such as anxiety states, emesis, schizophrenia and depressions as well as in certain motoric disorders, such as in Parkinson's disease, but also in inflammatory diseases, such as in rheumatoid arthritis, iritis and conjunctivitis, in diseases of the respiratory organs, such as in asthma and chronic bronchitis, in diseases of the gastrointestinal tract, such as in ulcerative colitis and Crohn's disease, and in hypertension.

Many efforts are directed to advancing the development in the field of the substance P antagonists and to find, for example, suitable substance P antagonists having a broader spectrum of activity as well as enhanced activity and enhanced bioavailability and also improved chemical stability and crystallinity.

Extensive pharmacological tests have shown that the novel compounds and the salts thereof antagonize substance P to a particularly preferred degree and are therefore particularly suited for the treatment of the symptoms caused by substance P.

The substance P-antagonizing effects can be detected, for example as shown hereinafter, by using test methods known to the expert. Such effects are found in vitro as well as in vivo. In the radioreceptor assay according to H. Bittiger, Ciba Foundation Symposium 91 (1982) 196–199, the compounds of formula I, for example, inhibit the bonding of $^3$H substance P to the bovine retina to an unexpectedly high degree, with $IC_{50}$ values from about 5 nM.

The formation of phosphoinositol in the human astrocytoma cells induced by substance P is, for example, also antagonized in vitro, resulting in $IC_{50}$ values from about 1 nM. A suitable test model for the detection of this inhibition is, for example, that of C. M. Lee et al., described in J. Neurochem. 59 (1992) 406–414.

The i.c.v.-administration of substance P methyl ester in gerbils results in abnormal behaviour. This effect can be inhibited upon peroral administration of compounds of formula I in vivo. The test method used is the process of A. Vassout et al. which was presented at the congress "Substance P and Related Peptides: Cellular and Molecular Physiology" in Worchester, Mass. 1990. $ED_{50}$ values from about 0.1 mg/kg p.o. were demonstrated there. These data establish the excellent suitablility of the compounds of formula I for the treatment of disorders of the central nervous system.

In comparison with the NK1 or substance P antagonists known so far, the novel compounds have markedly higher activity and also substantially higher chemical stability, e.g. to oxygen, enhanced crystallinity as well as improved oral bioavailability.

Accordingly, the substance P antagonists of formula I provided by this invention are excellently suited for the therapeutic treatment of the pathological symptoms indicated above.

The invention relates in particular to those compounds of formula I wherein ring A is unsubstituted or monosubstituted by halogen and ring B is unsubstituted or substituted by 1–2 substituents selected from the group consisting of lower alkyl, hydroxy, lower alkoxy, lower alkylthio, halogen, nitro and cyano, as well as to pharmaceutically acceptable salts thereof.

The invention relates primarily to those compounds of formula I wherein ring A is unsubstituted or chloro-monosubstituted and ring B is unsubstituted or substituted by 1–2 substituents selected from the group consisting of hydroxy, lower alkoxy, chloro and bromo, as well as to pharmaceutically acceptable salts thereof.

The invention relates in particular to those compounds of formula I wherein ring A is unsubstituted or monosubstituted by chloro and ring B is unsubstituted or monosubstituted by chloro or fluoro, as well as to pharmaceutically acceptable salts thereof.

Subgroups of a group of compounds of formula I to be highlighted each are: (a) compounds of formula I, wherein ring A is unsubstituted or substituted in 4-position by chloro; (b) compounds of formula I, wherein ring A is substituted in 4-position by chloro; (c) compounds of formula I, wherein ring B is monosubstituted by chloro or fluoro; (d) compounds of formula I, wherein ring B is unsubstituted.

The invention relates in particular to the specific compounds described in the Examples and salts, in particular pharmaceutically acceptable salts, thereof.

The compounds of formula I can be prepared in a manner known per se, typically by reacting a) a compound of formula IIa

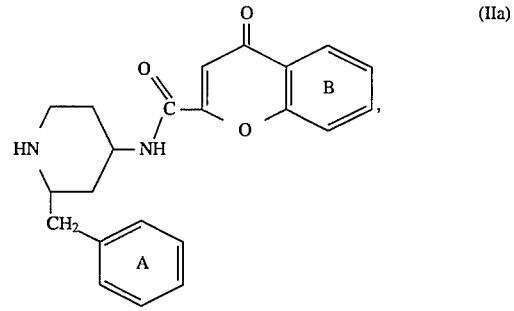

wherein rings A and B are as defined for formula I, with a compound of formula IIb

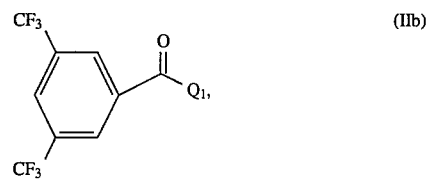

wherein $Q_1$ is hydroxy which may be etherified, e.g. hydroxy, lower alkoxy or unsubstituted or substituted phenoxy, or reactive esterified hydroxy, e.g. halogen, preferably chloro, or a radical of formula

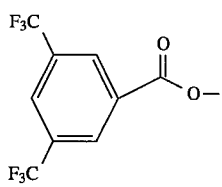

or a salt thereof; or by reacting
b) a compound of formula IIIa

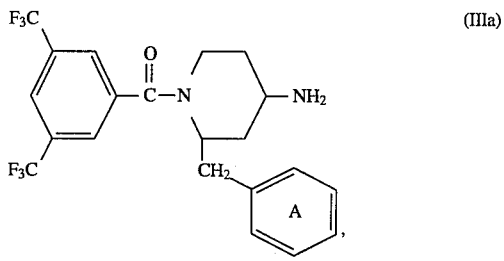

wherein ring A is as defined for formula I, with a compound of formula IIIb

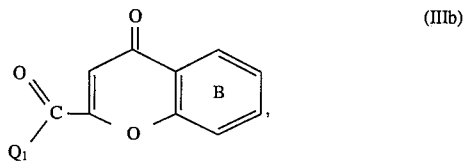

wherein ring B is as defined for formula I and $Q_1$ is hydroxy which may be etherified, e.g. hydroxy, lower alkoxy or unsubstituted or substituted phenoxy, or reactive esterified hydroxy, e.g. halogen, preferably chloro, or a radical of formula

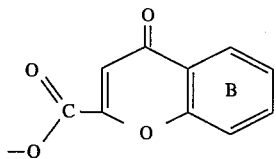

or a salt thereof;
and, if desired, converting a compound of formula I into another compound of formula I and/or, if desired, converting a salt obtained into the free compound or into another salt and/or, if desired, converting a free compound of formula I obtained having salt-forming properties into a salt and/or, if desired, separating a mixture of stereoisomers or diastereoisomers obtained into the individual stereoisomers and diastereoisomers.

Salts of starting materials having at least one basic center, e.g. those of formula IIa or IIIa, are corresponding acid addition salts, while salts of starting materials containing an acidic group, e.g. those of formula IIb or IIIb, are salts with bases.

In the following detailed description of the processes, rings A and B each have the meaning indicated for formula I, unless otherwise stated.

The reactions described in the variants hereinbefore and hereinafter are carried out in a manner known per se, typically in the absence or, usually, in the presence of a suitable solvent or diluent or of a mixture thereof and, depending on the requirements, with cooling, at room temperature or with heating, typically in the temperature range from about −80° C. to the boiling temperature of the reaction medium, preferably from about −10° to about +200° C. and, if required, in a closed vessel, under pressure, in an inert gas atmosphere and/or under anhydrous conditions.

Process variants a) and b): The condensation for the preparation of the respective amide bond can be carried out in a manner known per se, for example as described in standard works such as "Houben-Weyl, Methoden der organischen Chemie", 4th edition, Vol. 15/11, Georg Thieme Verlag, Stuttgart 1974, "The Peptides" (ed. E. Gross and J. Meienhofer), Vol. 1 and 2, Academic Press, London and New York, 1979/1980, or M. Bodanszky, "Principles of Peptide Synthesis", Springer-Verlag, Berlin 1984.

The condensation can be carried out in the presence of one of the customary condensing agents. Customary condensing agents are typically carbodiimides, e.g. diethylcarbodiimide, dipropylcarbodiimide, N-ethyl-N'-(3-dimethylaminopropyl)carbodiimide or, preferably, dicyclohexylcarbodiimide, and also suitable carbonyl compounds, typically carbonyldiimidazole, 1,2-oxazolium compounds, typically 2-ethyl-5-phenyl-1,2-oxazolium-3'-sulfonate and 2-tert-butyl-5-methylisoxazoliumperchlorate, or a suitable acylamino compound, typically 2-ethoxy-1-ethoxycarbonyl-1,2-dihydroquinoline, and also activated phosphoric acid derivatives, typically diphenylphosphorylazide, diethylphosphorylcyanide, phenyl-N-phenylphosphoramidochloridate, bis(2-oxo-3-oxazolidinyl)phosphinic acid chloride or 1-benzotriazolyloxytris-(dimethylamino)phosphoniumhexafluorophosphate.

If desired, an organic base is added such as a trilower alkyl amine containing voluminous radicals, e.g. ethyldiisopropylamine, or a heterocyclic base, typically pyridine, 4-dimethylaminopyridine or, preferably, N-methylmorpholine.

The condensation of an acyl halide, e.g. with a corresponding amine, can also be carried out in the presence of a suitable base without addition of a suitable coupling component.

The condensation is preferably carried out in an inert polar aprotic, preferably anhydrous, solvent or solvent mixture, typically in a carboxamide, e.g. formamide or dimethylformamide, in a halogenated hydrocarbon, e.g. methylene chloride, carbon tetrachloride or benzene chloride, in a ketone, e.g. acetone, in a cyclic ether, e.g. tetrahydrofuran, in an ester, e.g. ethyl acetate, or in a nitrile, e.g. acetonitrile, or in mixtures thereof, at low or elevated temperature, typically in a temperature range of about −40° C. to about +100° C., preferably from about −10° C. to about +50° C. and, optionally, under an inert gas atmosphere, e.g. under nitrogen.

Reactive acid derivatives can also be formed in situ.

The starting materials of formulae IIb and IIIb are known or can be prepared in a manner known per se.

Compounds of formula IIIa can be prepared in a manner known per se, starting e.g. from a compound of formula IIIc

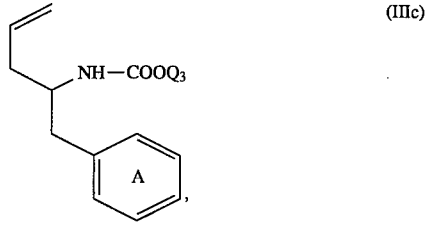

wherein $Q_3$ is e.g. lower alkyl or phenyl-lower alkyl. This compound is N-alkylated, typically by reaction with lower alkoxyhalomethane, such as ethoxychloromethane, in the presence of a base. The resulting compound of formula (IIId)

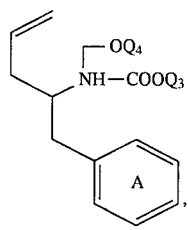

wherein $Q_4$ is e.g. lower alkyl, is treated with a nitrile, typically acetonitrile, in the presence of a strong acid, typically chlorosulfonic acid. In the resulting compound of formula IIIe

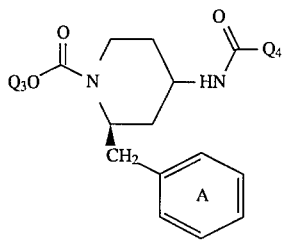

the —C(=O)—OQ$_3$ group is removed by treatment with a strong acid, typically hydrobromic acid.

For the preparation of an enantiomerically pure compound, the secondary amino group in a compound of formula IIIf

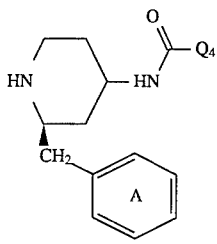

thus obtainable is acylated with an optically active compound, typically a corresponding O-acylated α-hydroxycarboxylic acid or a reactive derivative thereof, e.g. O-acetyl-(+)mandelic chloride, and the diastereoisomer mixture thus obtained is separated in a manner known per se, e.g. by chromatography. A compound of formula IIIg:

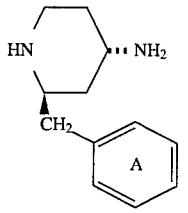

is obtained after removal of the two N-acyl groups, typically by acid hydrolysis, e.g. with hydrochloric acid. The 4-amino group of compounds of formula IIIg is temporarily protected in a manner known per se, typically by reaction with benzaldehyde. The 3,5,-bistrifluoromethylbenzoyl group is then introduced, e.g. as described for the process variant a), by coupling with a compound of formula IIb, and the protective group is then removed, typically by treatment with an acid, such as hydrochloric acid, resulting in a corresponding compound of formula IIIa.

Compounds of formula IIa can be prepared in a manner known per se, typically by starting from a compound of formula IIIg and coupling it, as described e.g. for the process variant b), with a compound of formula IIIb in the presence of a coupling reagent and thus introducing the corresponding acyl group. The corresponding compound of formula IIa is so obtained.

Salts obtained can be converted in a manner known per se into the free compounds, typically by treatment with a base, e.g. with an alkali metal hydroxide, a metal carbonate or metal hydrogen carbonate, or ammonia, or with another salt-forming base mentioned at the outset or with an acid, typically with a mineral acid, such as hydrogen chloride, or with another salt-forming acid mentioned at the outset.

Salts obtained can be converted in a manner known per se into other salts; in the case of acid addition salts typically by treatment with a suitable metal salt, e.g. a sodium, barium or silver salt, of another acid in a suitable solvent in which a resultant inorganic salt is insoluble and is thus eliminated from the equilibrium of reaction, and in the case of salts of bases by generating the free acid and repeated salt-formation.

The compounds of formula I, including their salts, can also be obtained in the form of hydrates or may also include the solvent used for crystallisation.

Because of the close relationship between the novel compounds in the free form and in the form of their salts, the references made throughout this specification to the free compounds and their salts will also apply by analogy to the corresponding salts or free compounds.

Because of the physicochemical differences of their components, the diastereoisomer and racemate mixtures obtained can be separated into the pure diastereoisomers and racemates in known manner, typically by chromatography and/or fractional crystallisation.

Resulting racemates can furthermore be separated by known methods into the optical antipodes, typically by recrystallisation from an optically active solvent, using microorganisms or by reacting the resulting diastereisomer mixture or racemate with an optically active auxiliary compound for example, depending on the acidic, basic or functionally modifiable groups present in the compounds of formula I, with an optically active acid, base or with an optically active alcohol, into mixtures of diastereisomeric salts and functional derivatives such as esters, separating these into the diastereoisomers from which the respective desired enantiomer can be set free in the respective usual manner. Bases, acids and alcohols suitable for the purpose are typically optically active alkaloid bases such as strychnine, cinchonine or brucine, or D- or L-(1-phenyl)ethylamine, 3-pipecoline, ephedrine, amphetamine and similar bases which are obtainable by synthesis, optically active carboxylic or sulfonic acids such as quinic acids or D- or L-tartaric acid, D- or L-di-o-toluyltartaric acid, D- or L-malic acid, D- or L-mandelic acid, or D- or L-camphorsulfonic acid, or optically active alcohols, e.g. borneol or D- or L-(1-phenyl)ethanol.

The invention also relates to those embodiments of the process in which a compound obtainable as intermediate at any stage of the process is used as starting material and the remaining steps are carried out, or a starting material is used in the form of a salt or, preferably, is formed under the reaction conditions.

The invention also relates to the novel starting materials which have been specially developed for the preparation of the novel compounds, especially those which result in the compounds of formula I described at the outset as being particularly preferred, to the processes for their preparation and to the use thereof as intermediates.

The novel compounds of formula I can be used, for example, in the form of pharmaceutical compositions containing a therapeutically effective amount of the active ingredient, if appropriate together with inorganic or organic, solid or liquid, pharmaceutically acceptable carriers suitable for enteral, e.g. oral, or parenteral administration. Accordingly, tablets or gelatin capsules are used that contain the active ingredient together with diluents, typically lactose, dextrose, saccharose, mannitol, sorbitol, cellulose and/or lubricants, e.g. diatomaceous earth, talcum, stearic acid or salts thereof, such as magnesium stearate or calcium stearate, and/or polyethylene glycol. Tablets may also contain binders, typically magnesium aluminium silicate, starches, typically corn starch, wheat starch, rice starch or arrow root starch, gelatin, tragacanth, methylcellulose, sodium carboxymethylcellulose and/or polyvinylpyrrolidone, and, if desired, disintegrators, typically starches, agar, alginic acid or a salt thereof, e.g. sodium alginate, and/or effervescent mixtures, or absorbents, colourants, flavourings and sweeteners. The novel compounds of formula I can also be used in the form of compositions for parenteral administration or infusion solutions. Such solutions are preferably isotonic aqueous solutions or suspension which, e.g. in the case of lyophilised compositions that contain the active ingredient by itself or together with a carrier, such as mannitol, can be prepared before use. The pharmaceutical compositions can be sterilised and/or can contain excipients, typically preservatives, stabilisers, wetting agents and/or emulsifiers, solubilisers, salts for regulating the osmotic pressure and/or buffers. The pharmaceutical compositions so obtained which, if desired, contain further pharmacologically active substances, are prepared in a manner known per se by conventional mixing, granulating, sugar-coating, solution or lyophilising methods and contain from about 0.1% to 100%, preferably from about 1% to about 50%, lyophilisate to about 100%, of active ingredient.

The invention also relates to the use of the compounds of formula I, preferably in the form of pharmaceutical compositions. The dosage can depend on a variety of factors, such as mode of application, species, age and/or individual state. In the case of oral administration, the daily doses are in the range from about 0.25 to about 10 mg/kg and for warm-blooded animals weighing about 70 kg they are preferably in the range from about 20 mg to about 500 mg.

The invention is illustrated by the following Examples wherein temperatures are given in degrees Celsius and pressures in mbar. FD-MS=field desorption mass spectroscopy.

Example 1: (2R,4S)-N-[1-(3,5-bistrifluoromethylbenzoyl)-2-(4-chlorobenzyl)piperidin-4-yl]-4-oxo-4H-1-benzopyrane-2-carboxamide 3.77 ml of triethylamine and 2.35 g of 4-oxo-4H-1-benzopyrane-2-carboxylic acid chloride (obtained from the corresponding carboxylic acid, supplied e.g. by Sigma, by reaction with thionyl chloride) are added to a solution of 4.36 g of (2R,4S)-4-amino-1-(3,5-bistrifluoromethylbenzoyl)-2-(4-chlorobenzyl)piperidine in 200 ml of methylene chloride and the mixture is stirred for 4 hours at 20°. The reaction mixture is washed with 1N aqueous hydrochloric acid and then with brine and water, dried over magnesium sulfate and concentrated by evaporation. The foam obtained is crystallised from tert-butylmethyl ether/hexane/methylene chloride, giving the title compound in the form of colourless crystals, m.p. 211°–212°.

$[\alpha]_D^{20}$=3.7±2.6 (c=0.382, methanol).

The starting compound can be prepared as follows:

a) N-[1-(4-chlorobenzyl)but-3-enyl]-N-ethoxymethylcarbamic acid methyl ester: A suspension of 10.0 g of sodium hydride (80% in mineral oil, 333 mmol) in anhydrous tetrahydrofuran [THF] is refluxed under argon. A solution of 60.5 g (238 mmol) of [1-(4-chlorobenzyl)but-3-enyl]carbamic acid methyl ester [McCarty F J et al., J. Med. Chem, 1968, 11(3),534] in 50 ml of anhydrous THF is added dropwise over 1 hour. The mixture is then refluxed for 2 hours until the evolution of gas subsides. The mixture is cooled to 0° C. and chloromethyl ethyl ether is added dropwise such that the reaction temperature does not rise above 5° C. The mixture is then slowly heated to 25° C. and stirred for 12 hours. Excess sodium hydride is carefully destroyed with 1 ml of water before more water is added. The phases are separated and the aqueous phase is extracted with tert-butylmethyl ether. The combined organic phases are washed with brine, dried over sodium sulfate and concentrated by evaporation. The crude product is distilled at 0.1 mbar and has a boiling range from 120° to 125° C. DC: ethyl acetate/hexane (1:6) $R_f$=0.34, FD-MS: M$^+$=311 (313).

b) (2R*,4S*)-4-acetylamino-2-(4-chlorobenzyl)piperidine-1-carboxylic acid methyl ester:

20.6 (308 mmol) of chlorosulfonic acid are added to 500 ml of acetonitrile at –40° C. A solution of 48.0 g (154 mmol) of N-[1-(4-chlorobenzyl)but-3-enyl]-N-ethoxymethylcarbamic acid methyl ester in 50 ml of acetonitrile is added dropwise to this mixture such that the reaction temperature does not rise above –10° C. The reaction mixture is then stirred for 20 minutes at –15° C. before adding 370 ml of 2N sodium hydroxide solution and 100 ml of a 10% solution of aqueous sodium hydrogen carbonate. The phases are separated and the aqueous phase is extracted twice with toluene. The combined organic phases are dried over sodium sulfate. The crude product is crystallised from toluene, giving the title compound in the form of white crystals. M.p.: 169°–170° C. DC: methylene chloride/methanol/conc. ammonia (90:9:1) $R_f$=0.42, FD-MS: M$^+$=325.

c) (2R*,4S*) N-[2-(4-chlorobenzyl)piperidin-4-yl]acetamide: 51.8 ml of 33% hydrogen bromide in acetic acid are added to (2R*,4S*)-4-acetylamino-2-(4-chlorobenzyl)piperidine-1-carboxylic acid methyl ester (30.0 g, 92.3 mmol). After 16 hours, 200 ml of water are added to the mixture which is then washed twice with toluene. The aqueous phase is basified and extracted twice with ethyl acetate. The organic phases are dried over potassium and concentrated by evaporation on a rotary evaporator. The title compound crystallises as hydrochloride from ethanol/ethyl acetate. M.p.: 288°–289° C. DC: methylene chloride/methanol/conc. ammonia (90:9:1) $R_f$=0.17, FD-MS: (M+1)$^+$=267.

d) (2'S,2R,4S)acetic acid-2-[4-acetylamino-2-(4-chlorobenzyl)piperidin-1-yl]-2-oxo-1-phenyl ethyl ester: Racematic N-[2-(4-chlorobenzyl)piperidin-4-yl]acetamide hydrochloride (20.5 g, 67.6 mmol) is added at 0° C., with vigorous stirring, to 34 ml of 2N sodium hydroxide solution, 150 ml of a 10% solution of aqueous sodium hydrogen carbonate and 50 ml of methylene chloride. S(+)-O-acetylmandelic acid chloride [Pracejus G, Ann., 1959, 622, 10] (14.9 g, 70 mmol) is added dropwise over 1 hour. The mixture is then stirred for 1 hour at +4° C. The phases are separated and the organic phase is dried over sodium sulfate and concentrated by evaporation on a rotary evaporator. After crystallising twice from methylene chloride/tert-butylmethyl ether, the title compound is isolated as pure diastereoisomer. M.p.: 209°–211° C. DC: methylene chloride/isopropanol (9:1) $R_f$=0.65, FD-MS: M$^+$=443. [alpha]$^D$= +77.5 degree (c=1, methylene chloride).

The mother liquors contain mainly the non-crystalline diastereoisomer (2'S,2S,4R)N-[2-(4-chlorobenzyl)-1-(acetoxyphenylacetyl)piperidin-4-yl]acetamide, DC: methylene chloride/isopropanol (9:1) $R_f$=0.70.

e) (2R,4S)-4-amino-1-(3,5-bistrifluoromethylbenzoyl)-2-(4-chlorobenzyl)piperidine:

(2'S,2R,4S)acetic acid-2-[4-acetylamino-2-(4-chlorobenzyl)piperidin-1-yl]-2-oxo-1-phenyl ethyl ester (37.4 g, 84.5 mmol) is refluxed for 2 days in 370 ml of 6N hydrochloric acid. After cooling, the mixture is basified with solid sodium hydroxide and extracted with methylene chloride. The combined organic phases are dried over potassium carbonate and concentrated by evaporation on a rotary evaporator. The residue, which consists of almost pure (2R,4S)-2-(4-chlorobenzyl)piperidine-4-amine (19.0 g, 84.5 mmol, 100%), is taken up in 8.5 ml (84.5 mmol) of benzaldehyde and concentrated twice with 150 ml of toluene on a rotary evaporator. The oily residue is taken up in 180 ml of methylene chloride and 15.3 ml (110 mmol) of triethylamine and cooled to 10° C. Bistrifluoromethylbenzoyl chloride (25.7 g, 92.9 mmol) is added dropwise over 15 minutes and the mixture is then stirred for 1 hour at 25° C. 250 ml of 1N hydrochloric acid are added to the reaction mixture and the methylene chloride is removed under reduced pressure on a rotary evaporator. Hexane and ethanol are added until two homogeneous phases are obtained. The organic phase is removed and the mixture is washed with hexane until the benzaldehyde is completely removed. The mixture is basified with solid sodium hydroxide and repeatedly extracted with sodium hydroxide. The organic phases are dried over sodium sulfate and concentrated on a rotary evaporator. Crystallisation from tert-butylmethyl ether/hexane gives the title compound in the form of white crystals. M.p.: 79°–81° C. DC: methylene chloride/methanol/conc. ammonia (90:9:1) $R_f$=0.21, FD-MS: (M+1)$^+$=465.

[alpha]$_D^{20}$=−12.7 Grad (c=1, methylene chloride).

The following compounds can also be prepared in accordance with the general procedure described in Example 1. The preparation of the corresponding starting material, (2R, 4S)-4-amino-1-(3,5-bistrifluoromethylbenzoyl)-2-benzylpiperidine, is described in EP-A-532 456, Example 38f:

Example 1/1: (2R,4S)-N-[1-(3,5-bistrifluoromethylbenzoyl)-2-benzylpiperidin-4-yl]-4-oxo-4H-1-benzopyrane-2-carboxamide, m.p. 107°–108°, [α]$_D^{20}$=18.3±2.6 (c=0.388, methanol)

Example 1/2: (2R,4S)-N-[1-(3,5-bistrifluoromethylbenzoyl)-2-benzylpiperidin-4-yl]-7-chloro-4-oxo-4H-1-benzopyrane-2-carboxamide, m.p. 224°–226°, [α]$_D^{20}$=21.5±2.5 (c=0.40, methanol)

Example 1/3: (2R,4S)-N-[1-(3,5-bistrifluoromethylbenzoyl)-2-benzylpiperidin-4-yl]-7-methoxy-4-oxo-4H-1-benzopyrane-2-carboxamide, m.p. 190°–192°, [α]$_D^{20}$=25.7±2.3 (c=0.44, methanol)

Example 1/4: (2R,4S)-N-[1-(3,5-bistrifluoromethylbenzoyl)-2-benzylpiperidin-4-yl]-7-methylthio-4-oxo-4H-1-benzopyrane-2-carboxamide Example 1/5: (2R,4S)-N-[1-(3,5-bistrifluoromethylbenzoyl)-2-benzylpiperidin-4-yl]-6-methoxy-4-oxo-4H-1-benzopyrane-2-carboxamide Example 1/6: (2R,4S)-N-[1-(3,5-bistrifluoromethylbenzoyl)-2-benzylpiperidin-4-yl]-6-chloro-4-oxo-4H-1-benzopyrane-2-carboxamide Example 1/7: (2R,4S)-N-[1-(3,5-bistrifluoromethylbenzoyl)-2-benzylpiperidin-4-yl]-6-bromo-4-oxo-4H-1-benzopyrane-2-carboxamide Example 1/8: (2R,4S)-N-[1-(3,5-bistrifluoromethylbenzoyl)-2-benzylpiperidin-4-yl]-6-fluoro-4-oxo-4H-1-benzopyrane-2-carboxamide Example 1/9: (2R,4S)-N-[1-(3,5-bistrifluoromethylbenzoyl)-2-benzylpiperidin-4-yl]-6-methyl-4-oxo-4H-1-benzopyrane-2-carboxamide Example 1/10: (2R,4S)-N-[1-(3,5-bistrifluoromethylbenzoyl)-2-benzylpiperidin-4-yl]-6-cyano-4-oxo-4H-1-benzopyrane-2-carboxamide Example 1/11: (2R,4S)-N-[1-(3,5-bistrifluoromethylbenzoyl)-2-benzylpiperidin-4-yl]-6-nitro-4-oxo-4H-1-benzopyrane-2-carboxamide Example 1/12: (2R,4S)-N-[1-(3,5-bistrifluoromethylbenzoyl)-2-benzylpiperidin-4-yl]-7-fluoro-4-oxo-4H-1-benzopyrane-2-carboxamide Example 1/13: (2R,4S)-N-[1-(3,5-bistrifluoromethylbenzoyl)-2-benzylpiperidin-4-yl]-7-bromo-4-oxo-4H-1-benzopyrane-2-carboxamide Example 1/14: (2R,4S)-N-[1-(3,5-bistrifluoromethylbenzoyl)-2-benzylpiperidin-4-yl]-7-methyl-4-oxo-4H-1-benzopyrane-2-carboxamide Example 1/15: (2R,4S)-N-[1-(3,5-bistrifluoromethylbenzoyl)-2-benzylpiperidin-4-yl]-7-nitro-4-oxo-4H-1-benzopyrane-2-carboxamide Example 1/16: (2R,4S)-N-[1-(3,5-bistrifluoromethylbenzoyl)-2-benzylpiperidin-4-yl]-6,7-dimethoxy-4-oxo-4H-1-benzopyrane-2-carboxamide.

Example 2: (2R,4S)-N-[1-(3,5-bistrifluoromethylbenzoyl)-2-benzylpiperidin-4-yl]-7-hydroxy-4-oxo-4H-1-benzopyrane-2-carboxamide A solution of 0.127 g (2R,4S)-4-amino-1-(3,5-bistrifluoromethylbenzoyl)-2-benzylpiperidine in 3.1 ml of methylene chloride is taken up in 0.038 g of 4-dimethylaminopyridine, 0.059 g N-(3-dimethylaminopropyl)-N'-ethylcarbodiimide hydrochloride and 0.064 g of 7-hydroxy-4-oxo-4H-1-benzopyrane-2-carboxylic acid in 2 ml of methylene chloride/dimethylformamide (1:1) and stirred for 24 hours at 20°. The reaction mixture is concentrated by evaporation and the residue is chromatographed on silica gel with methylene chloride and methylene chloride/methanol (19:1), giving the title compounds in the form of a pale yellow powder having an m.p. of 224°–225°; [α]$_D^{20}$= 23.3±3.5 (c=0.288, methanol).

The following compound can also be prepared in accordance with the general procedure described in Example 2:

Example 2/1: (2R,4S)-N-[1-(3,5-bistrifluoromethylbenzoyl)-2-benzylpiperidine-4-yl]-6-bromo-7-hydroxy-4-oxo-4H-1-benzopyrane-2-carboxamide. M.p.: 173°–174°.

Example 3: The following compounds can also be prepared in accordance with the general procedure described in Example 1, starting from (2R,4S)-4-amino-1-(3,5-bistrifluoromethyl-benzoyl)-2-(4-chlorobenzyl)piperidine [Example 1 e)]:

Example 3/1: (2R,4S)-N-[1-(3,5-bistrifluoromethylbenzoyl)-2-(4-chlorobenzyl)piperidin-4-yl]-7-chloro-4-oxo-4H-1-benzopyrane-2-carboxamide. M.p.: 218°–220°, [α]$_D^{20}$=31.5±2.0 (c=0.50, methanol).

Example 3/2: (2R,4S)-N-[1-(3,5-bistrifluoromethylbenzoyl)-2-(4-chlorobenzyl)piperidin-4-yl]-7-methoxy-4-oxo-4H-1-benzopyrane-2-carboxamide. M.p.: 198°–200°, [α]$_D^{20}$=29.7±2.2 (c=0.45, methanol).

Example 3/3: (2R,4S)-N-[1-(3,5-bistrifluoromethylbenzoyl)-2-(4-chlorobenzyl)piperidin-4-yl]-7-methylthio-4-oxo-4H-1-benzopyrane-2-carboxamide. M.p.: 137°–140°, [α]$_D^{20}$=20.8±2.8 (c=0.355, methanol).

Example 3/4: (2R,4S)-N-[1-(3,5-bistrifluoromethylbenzoyl)-2-(4-chlorobenzyl)piperidin-4-yl]-6-methoxy-4-oxo-4H-1-benzopyrane-2-carboxamide.

Example 3/5: (2R,4S)-N-[1-(3,5-bistrifluoromethylbenzoyl)-2-(4-chlorobenzyl)piperidin-4-yl]-6-chloro-4-oxo-4H-1-benzopyrane-2-carboxamide.

Example 3/6: (2R,4S)-N-[1-(3,5-bistrifluoromethylbenzoyl)-2-(4-chlorobenzyl)piperidin-4-yl]-6-bromo-4-oxo-4H-1-benzopyrane-2-carboxamide.

Example 3/7: (2R,4S)-N-[1-(3,5-bistrifluoromethylbenzoyl)-2-(4-chlorobenzyl)piperidin-4-yl]-6-fluoro-4-oxo-4H-1-benzopyrane-2-carboxamide. M.p.: 215°–218°; $R_f$ (ethyl acetate/hexane 4:1)=0.58. The acid chloride 6-fluoro-4-oxo-4H-1-benzopyrane-2-carboxylic acid chloride required as starting material is described, inter alia, in Chemical Abstracts: 96:52132w or 88:106066w and has the CAS Reg. No. 65843-87-0.

Example 3/8: (2R,4S)-N-[1-(3,5-bistrifluoromethylbenzoyl)-2-(4-chlorobenzyl)piperidin-4-yl]-6-methyl-4-oxo-4H-1-benzopyrane-2-carboxamide. M.p.: 240°–241°; $R_f$ (ethyl acetate/hexane 4:1)=0.65.

Example 3/9: (2R,4S)-N-[1-(3,5-bistrifluoromethylbenzoyl)-2-(4-chlorobenzyl)piperidin-4-yl]-6-cyano-4-oxo-4H-1-benzopyrane-2-carboxamide.

Example 3/10: (2R,4S)-N-[1-(3,5-bistrifluoromethylbenzoyl)-2-(4-chlorobenzyl)piperidin-4-yl]-6-nitro-4-oxo-4H-1-benzopyrane-2-carboxamide.

Example 3/11: (2R,4S)-N-[1-(3,5-bistrifluoromethylbenzoyl)-2-(4-chlorobenzyl)piperidin-4-yl]-7-fluoro-4-oxo-4H-1-benzopyrane-2-carboxamide.

Example 3/12: (2R,4S)-N-[1-(3,5-bistrifluoromethylbenzoyl)-2-(4-chlorobenzyl)piperidin-4-yl]-7-bromo-4-oxo-4H-1-benzopyrane-2-carboxamide.

Example 3/13: (2R,4S)-N-[1-(3,5-bistrifluoromethylbenzoyl)-2-(4-chlorobenzyl)piperidin-4-yl]-7-methyl-4-oxo-4H-1-benzopyrane-2-carboxamide.

Example 3/14: (2R,4S)-N-[1-(3,5-bistrifluoromethylbenzoyl)-2-(4-chlorobenzyl)piperidin-4-yl]-7-nitro-4-oxo-4H-1-benzopyrane-2-carboxamide.

Example 3/15: (2R,4S)-N-[1-(3,5-bistrifluoromethylbenzoyl)-2-(4-chlorobenzyl)piperidin-4-yl]-6,7-dimethoxy-4-oxo-4H-1-benzopyrane-2-carboxamide.

Example 4: Tablets containing 50 mg of active ingredient each can be prepared as follows:

| Composition (10000 tablets) | |
| --- | --- |
| active ingredient | 500.0 g |
| lactose | 500.0 g |
| potato starch | 352.0 g |
| gelatin | 8.0 g |
| talcum | 60.0 g |
| magnesiume stearate | 10.0 g |
| silicium dioxide (highly dispersed) | 20.0 g |
| ethanol | q.s. |

The active ingredient is mixed with the lactose and 292 g of potato starch and the mixture is then moistened with an ethanolic solution of the gelatin and granulated through a sieve. After drying, the remainder of the potato starch, the magnesium stearate, the talcum and the silicium dioxide are admixed and the mixture is pressed to tablets weighing 145.0 mg each and having an active ingredient content of 50.0 mg. If desired, the tablets may have dividing notches to permit finer adjustment of the dose.

Example 5: Film-coated tablets containing 100 mg of active ingredient each can be prepared as follows:

| Composition (for 1000 film-coated tablets) | |
| --- | --- |
| active ingredient | 100.0 g |
| lactose | 100.0 g |
| corn starch | 70.0 g |
| talcum | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed and moistened with a paste prepared from 15 g of corn starch and water (with heating) and granulated. The granulate is dried and the remainder of the corn starch, the talcum and the calcium stearate are added and mixed with the granulate. The mixture is pressed to tablets (weight: 280 mg) which are then coated with a solution of the hydroxypropylmethylcellulose and the shellac in methylene chloride. End weight of the film-coated tablet: 283 mg.

Example 6: Gelatin dry-filled capsules containing 100 mg of active ingredient can be prepared, for example, as follows:

| Composition (for 1000 capsules) | |
| --- | --- |
| active ingredient | 100.0 g |
| lactose | 250.0 g |
| microcrystalline cellulose | 30.0 g |
| sodium laurylsulfate | 2.0 g |
| magnesium stearate | 8.0 g |

The sodium laurylsulfate is added by sieving through a sieve having a mesh size of 0.2 mm to the lyophilised active ingredient. Both components are intimately mixed. Subsequently the lactose is added first by sieving through a sieve having a mesh size of 0.6 mm and then the microcrystalline cellulose by added by sieving through a sieve having a mesh size of 0.9 mm. The mixture is again intimately mixed for 10 minutes. The magnesium stearate is added last by sieving through a sieve having a mesh size of 0.8 mm. After a further mixing of 3 minutes, 390 mg each of the formulation so obtained are filled into gelatin dry-filled capsules of size 0.

Example 7: An propellant-containing inhalation suspension containing 0.1% by weight of active ingredient:

| Composition | % by weight |
| --- | --- |
| active ingredient, micronised | 0.1 |
| sorbitantrioleate | 0.5 |
| propellant A (trichlorotrifluorothane) | 4.4 |
| propellant B (dichlorodifluoromethane and 1,2-dichlorotetrafluorothane) | 15.0 |
| | 80.0 |

Using one of the conventional homogenisers, the active ingredient is suspended, excluding humidity, with the addition of the sorbitantrioleate in the trichlorotrifluorothane, and the suspension is then filled into an aerosol container equipped with a dosing valve. The container is closed and filled under pressure with the propellant B.

What is claimed is:

1. A compound of formula I

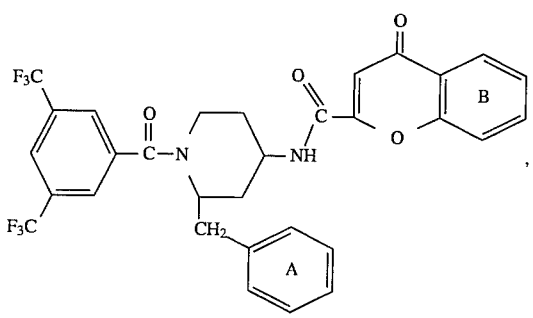

wherein ring A is unsubstituted or monosubstituted by lower alkyl, lower alkoxy, halogen, nitro or trifluoromethyl and ring B is unsubstituted or substituted by 1–4 substituents selected from the group consisting of lower alkyl, hydroxy, lower alkoxy, lower alkylthio, halogen, nitro, cyano and trifluoromethyl, or a salt thereof.

2. A compound of formula I according to claim 1, wherein ring A is unsubstituted or monosubstituted by halogen and ring B is unsubstituted or substituted by 1–2 substituents selected from the group consisting of lower alkyl, hydroxy, lower alkoxy, lower alkylthio, halogen, nitro and cyano, or a pharmaceutically acceptable salt thereof.

3. A compound of formula I according to claim 1, wherein ring A is unsubstituted or monosubstituted by chloro and ring B is unsubstituted or substituted by 1–2 substituents selected from the group consisting of hydroxy, lower alkoxy, chloro and bromo, or a pharmaceutically acceptable salt thereof.

4. A compound of formula 1 according to claim 1, wherein ring A is unsubstituted or monosubstituted by chloro and ring B is unsubstituted or monosubstituted by chloro or fluoro, or a pharmaceutically acceptable salt thereof.

5. A compound of formula I according to claim 1, wherein the compound of formula I is in the diastereoisomeric form as represented in formula Ia:

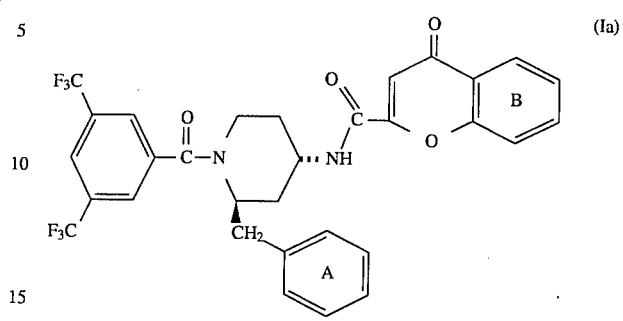

6. (2R,4S )-N-[1-(3,5-bistrifluoromethylbenzoyl)-2-(4-chlorobenzyl)piperidin-4-yl]-4-oxo-4H-1-benzopyrane-2-carboxamide according to claim 1 or a pharmaceutically acceptable salt thereof.

7. (2R,4S)-N-[1-(3,5-bistrifluormethylbenzoyl)-2-benzylpiperidin-4-yl]-4-oxo-4H-1-benzopyrane-2-carboxamide according to claim 1 or a pharmaceutically acceptable salt thereof.

8. (2R,4S)-N-[1-(3,5-bistrifluoromethylbenzoyl)-2-(4-chlorobenzyl)piperidin-4-yl]-6-fluoro-4-oxo-4H-1-benzopyrane-2-carboxamide according to claim 1 or a pharmaceutically acceptable salt thereof.

9. A pharmaceutical composition comprising a therapeutically effective amount of a compound according to claim 1 and at least one pharmaceutically acceptable carrier.

10. A method of treating diseases responsive to an antagonisation of the NK1 receptor, which method comprises administering to a mammal in need thereof a therapeutically effective amount of a compound of formula I according to claim 1 or a pharmaceutically acceptable salt thereof.

* * * * *